US009192644B2

(12) United States Patent
Frautschy et al.

(10) Patent No.: US 9,192,644 B2
(45) Date of Patent: Nov. 24, 2015

(54) BIOAVAILABLE CURCUMINOID FORMULATIONS FOR TREATING ALZHEIMER'S DISEASE AND OTHER AGE-RELATED DISORDERS

(75) Inventors: Sally A. Frautschy, Santa Monica, CA (US); Gregory M. Cole, Santa Monica, CA (US)

(73) Assignees: The Regents of the University of California, Oakland, CA (US); Department of Veterans Affairs, Washington, DC (US)

( * ) Notice: Subject to any disclaimer, the term of this patent is extended or adjusted under 35 U.S.C. 154(b) by 1092 days.

(21) Appl. No.: 12/225,005

(22) PCT Filed: Mar. 6, 2007

(86) PCT No.: PCT/US2007/005829
§ 371 (c)(1),
(2), (4) Date: Apr. 3, 2009

(87) PCT Pub. No.: WO2007/103435
PCT Pub. Date: Sep. 13, 2007

(65) Prior Publication Data
US 2009/0324703 A1 Dec. 31, 2009

Related U.S. Application Data

(60) Provisional application No. 60/779,817, filed on Mar. 6, 2006.

(51) Int. Cl.
*A61K 9/127* (2006.01)
*A61K 31/235* (2006.01)
*A61K 36/9066* (2006.01)

(52) U.S. Cl.
CPC .................................. *A61K 36/9066* (2013.01)

(58) Field of Classification Search
CPC ................................................ A61K 36/9066
USPC .......................................... 424/450; 514/679
See application file for complete search history.

(56) References Cited

U.S. PATENT DOCUMENTS

| | | | | |
|---|---|---|---|---|
| 4,263,333 | A * | 4/1981 | Maing et al. | 426/540 |
| 6,979,441 | B2 * | 12/2005 | Crandall | 424/78.06 |
| 2003/0147979 | A1 | 8/2003 | Mae et al. | |
| 2004/0001817 | A1 * | 1/2004 | Giampapa | 424/94.1 |
| 2005/0222250 | A1 * | 10/2005 | Rezvani | 514/461 |
| 2005/0239721 | A1 * | 10/2005 | Rosenbloom | 514/27 |
| 2006/0024374 | A1 | 2/2006 | Gasco et al. | |
| 2006/0045928 | A1 * | 3/2006 | Oshiro | 424/756 |
| 2008/0103213 | A1 * | 5/2008 | Kurzrock et al. | 514/679 |
| 2009/0131373 | A1 | 5/2009 | Giori et al. | |

FOREIGN PATENT DOCUMENTS

FR 2655054 A1 * 5/1991
WO WO 2004080396 A2 * 9/2004

OTHER PUBLICATIONS

Pan et al. Biotransformation of curcumin through reduction and glucuronidation in mice. Drug Metabolism and Disposition, Apr. 1999, vol. 27, No. 4, pp. 486-494.*
Shoba et al. Planta medica, vol. 64, Issue 4, pp. 353-356. 1998.*
Chen et al. Bioengineering Conference, 2005. Proceedings of the IEEE 31st Annual Northeast, Apr. 2-3, 2005, pp. 275-276.*
Ono, K. et al., Ferulic acid destablilizes preformed β-amyloid fibrils in vitro, Biochemical and Biophysical Research Communication, 336, 2005, pp. 444-449.
Liu, A. et al., Validated LC/MS/MS assay for curcumin and tetrahydrocurcumin in rat plasma and application to pharmacokinetic study of phospholipid complex of curcumin, Journal of Pharmaceutical and Biomedial Analysis, 40, 2006, pp. 720-727.
Weber, W. M., et al., Activation of NFκB is inhibited by curcumin and related enones, Bioorganic & Medicinal Chemistry, 14, 2006, pp. 2450-2461.
Ono, K., et al., Antioxidant compounds have potent anti-fibrillogenic and fibril-destabilizing effects for α-synuclein fibrils in vitro, Journal of Neurochemistry, 2006, vol. 97, pp. 105-115.
Ireson, C. et al., Characterization of Metabolites of the Chemopreventive Agent Curcumin in Human and Rat Hepatocytes and in the Rat in Vivo, and Evaluation of Their Ability to Inhibit Phorbol Ester-induced Prostaglandin $E_2$ Production, Cancer Research 61, Feb. 1, 2001, pp. 1058-1064.
Sharma, R.A. et al., Phase I Clinical Trial of Oral Curcumin: Biomarkers of Systemic Activity and Compliance, Clinical Cancer Research, vol. 10, Oct. 15, 2004, pp. 6847-6854.
Frautschy, S.A., Phenolic anti-inflammatory antioxidant reversal of Aβ-induced cognitive deficits and neuropathology, Neurobiology of Aging, 22, 2001, pp. 993-1005.
Yang, F., et al., Curcumin Inhibits Formation of Amyloid β Oligomers and Fibrils, Binds Plaques, and Reduces Amyloid in Vivo, The Journal of Biological Chemistry, vol. 280, No. 7, Issue Feb. 18, 2005, pp. 5892-5901.
Lim, G.P., et al., The Curry Spice Curcumin Reduces Oxidative Damage and Amyloid Pathology in an Alzheimer Transgenic Mouse, The Journal of Neuroscience, Nov. 1, 2001, 21(21) pp. 8370-8377.
Lao, C.D., et al., Dose escalation of a curcuminoid formulation, BMC Complementary and Alternative Medicine, 6:10, Mar. 17, 2006, 4 pgs.
Heath, D.D., et al., Tetrahydrocurcumin in plasma and urine: Quantitation by high performance liquid chromatography, Journal of Chromatography B, 824 (2005) pp. 206-212.
Begum, A.N., et al., Curcumin Structure-Function, Bioavailability, and Efficacy in Models of Neuroinflammation and Alzheimer's Disease, The Journal of Pharmacology and Experimental Therapeutics, vol. 326, No. 1, pp. 196-208 (2008).

(Continued)

*Primary Examiner* — Janet Epps-Smith
(74) *Attorney, Agent, or Firm* — Christie, Parker & Hale, LLP

(57) ABSTRACT

Curcuminoid formulations having enhanced bioavailability are provided and comprise a curcuminoid, antioxidant, glucuronidation inhibitor, and water-soluble, pharmaceutically acceptable inhibitor. A method of treating Alzheimer's and other age-related diseases by administering such a composition is also provided.

24 Claims, 14 Drawing Sheets

(56) References Cited

OTHER PUBLICATIONS

Garcia-Alloza, M., et al., Curcumin labels amyloid pathology in vivo, disrupts existing plaques, and partially restores distorted neurites in an Alzheimer mouse model, Journal of Neurochemistry, 2007, 10 pgs.

Saha, R.N., et al., Regulation of Inducible Nitric Oxide Synthase Gene in Glial Cells, Antioxid. Redox Signal 2006, 8(5-6) 30 pgs.

Marcu, M.G., et al., Curcumin is an Inhibitor of p300 Histone Acetylatransferase, Medicinal Chemistry, 2006, 2, pp. 169-174.

Baum, L., et al., Curcumin interaction with copper and iron suggests one possible mechanism of action in Alzheimer's disease animal models, Journal of Alzheimer Disease, 6, (2004) pp. 367-377.

Heath, D.D., et al., Curcumin in plasma and urine: quantitation by high performance liquid chromatography, Journal of Chromatography B, 783, (2003) pp. 287-295.

Yang, F., et al., Antibody to Caspase-Cleaved Actin Detects Apoptosis in Differentiated Neuroblastoma and Plaque-Associated Neurons and Microglia in Alzheimer's Disease, American Journal of Pathology, vol. 152, No. 2, Feb. 1998, pp. 379-389.

Aggarwal, B.B., et al., Anticancer Potential of Curcumin: Preclinical and Clinical Studies, Anticancer Research, vol. 23 (2003) pp. 363-398.

Caughey, B., et al., Inhibition of Protease-Resistant Prion Protein Accumulation in Vitro by Curcumin, Journal of Virology, May 2003, vol. 77, No. 9, pp. 5499-5502.

Ramaswami, G., M.D., PhD, et al., Curcumin blocks homocysteine-induced endothelial dysfunction in porcine coronary arteries, Journal of Vascular Surgery, vol. 40, No. 6, pp. 1216-1222, (2004).

Miquel, J., et al., The curcuma antioxidants: pharmacological effects and prospects for future clinical use. A Review, Archives of Gerontology and Geriatrics, vol. 34 (2002) pp. 37-46.

Rajakrishnan, V., et al., Neuroprotective Role of Curcumin from *Curcuma longa* on Ethanol-induced Brain Damage, Phytotherapy Research, vol. 13 (1999) pp. 571-574.

NCI, DCPC, Chemoprevention Branch and Agent Development Committee, Clinical Development Plan Curcumin, Journal of Cellular Biochemistry, vol. 265 (1996) pp. 72-85.

Chainani-Wu, N., D.M.D., M.P.H., M.S., Safety and Anti-Inflammatory Activity of Curcumin: A Component of Tumeric (*Curcuma longa*), The Journal of Alternative and Complementary Medicine, vol. 9, No. 1, 2003, pp. 161-168.

Garcea G., et al., Detection of curcumin and its metabolites in hepatic tissue and portal blood of patients following oral administration, British Journal of Cancer, (2004) vol. 90, pp. 1011-1015.

Basu, N.K., et al., Human UDP-Glucuronosyltransferases Show Atypical Metabolism of Mycophenolic Acid and Inhibition by Curcumin, Drug Metabolism and Disposition, 2004, vol. 32, No. 7, pp. 768-773.

Wang, Y., et al., Synthesis and preliminary antitumor activity evaluation of a DHA and doxorubicin conjugate, Bioorganic & Medicinal Chemistry Letters, 16 (2006) pp. 2974-2977.

Luo, Y., et al., Solid lipid nanoparticles for enhancing vinpocetine's oral bioavailability, Journal of Controlled Release, vol. 114 (2006) pp. 53-59.

Began, G., et al., Interaction of Curcumin with Phosphatidylcholine: A Spectrofluorometric Study, J. Agric. Food Chem., 1999, vol. 47, pp. 4992-4997.

Bradley, M.O., et al., Tumor Targeting by Covalent Conjugation of a Natural Fatty Acid to Paclitaxel, Clinical Cancer Research, vol. 7, Oct. 2001, pp. 3229-3238.

Bradley, M.O., et al., Tumor targeting by conjugation of DHA to paclitaxel, Journal of Controlled Release, vol. 74 (2001) pp. 233-236.

Harries, M., et al., Phase I/II study of DHA—paclitaxel in combination with carboplatin in patients with advanced malignant solid tumors, British Journal of Cancer, (2004) vol. 91, pp. 1651-1655.

Uchaipichat, V., et al., Human UDP-Glucuronosyltransferases: Isoform Selectivity and Kinetics of 4-Methylumbelliferone and 1-Naphthol Glucuronidation, Effects of Organic Solvents, and inhibition by Diclofenac and Probenecid, Drug Metabolism and Disposition, vol. 32, No. 4, pp. 413-423, (2004).

Vree, T.B., et al., Probenecid inhibits the glucuronidation of indomethacin and O-desmethylindomethacin in humans, Pharmacy World and Science, vol. 16, No. 1, 1994, pp. 22-26.

Wang, Y., et al., Stability of curcumin in buffer solutions and characterization of its degradation products, Journal of Pharmaceutical and Biomedical Analysis, vol. 15 (1997) pp. 1867-1876.

Hong, J., et al., Modulation of arachidonic acid metabolism by curcumin and related $\beta$-diketone derivatives: effects on cytosolic phospholipase $A_2$, cyclooxygenases and 5-lipoxygenase, Carcinogenesis, vol. 25, No. 9, 2004, pp. 1671-1679.

Chen, J., et al., Curcumin protects PC12 cells against 1-methyl-4-phenylpyridinium ion-induced apoptosis by bcl-2-mitochondria-ROS-iNOS pathway, Apoptosis, vol. 11, No. 6, 2006, pp. 943-953.

Osawa, T., et al., Antioxidative Activity of Tetrahydrocurcuminoids, Biosci, Biotech, Biochem, vol. 59, No. 9, 1995, pp. 1609-1612.

Ono, K., et al., Curcumin Has Potent Anti-Amyloidogenic Effects for Alzheimer's $\beta$-Amyloid Fibrils in Vitro, Journal of Neuroscience Research, vol. 75, 2004, pp. 742-750.

Kayed, R., et al., Permeabilization of Lipid Bilayers is a Common Conformation-dependent Activity of Soluble Amyloid Oligomers in Protein Misfolding Diseases, The Journal of Biological Chemistry, vol. 279, No. 45, Nov. 2004, pp. 46363-46366.

Asai, A., et al., Occurrence of orally administered curcuminoid as glucuronide and glucuronide/sulfate conjugates in rat plasma, Life Sciences, vol. 67, 2000, pp. 2785-2793.

Toothaker, R.D., et al., The Effect of Food on Drug Bioavailability, Annu. Rev. Pharmacol Taxicol, 980, vol. 20, pp. 173-199.

Ryu, E. K., et al., Curcumin and Dehydrozingerone Derivatives: Synthesis, Radiolabeling, and Evaluation for $\beta$-Amyloid Plaque Imaging, Journal of Medicinal Chemistry, 2006, vol. 49, pp. 6111-6119.

Mai, A., et al., Small-Molecule Inhibitors of Histone Acetyltransferase Activity: Identification and Biological Properties, Journal of Medicinal Chemistry, 2006, vol. 49, pp. 6897-6907.

Kim, J.E., et al., In Vitro Peroxynitrite Scavenging Activity of Diarylheptanoids from *Curcuma longa*, Phytotherapy Research, vol. 17, 2003, pp. 481-484.

Thiyagarajan, M., et al., Neuroprotective effect of curcumin in middle cerebral artery occlusion induced focal cerebral ischemia in rats, Life Sciences, vol. 74, 2004, pp. 969-985.

Cherny, R.A., et al., Treatment with a Cooper-Zinc Chelator Markedly and Rapidly Inhibits $\beta$-Amyloid Accumulation in Alzheimer's Disease Transgenic Mice, Neuron, vol. 30, Jun. 2001, pp. 665-676.

Kim, H., et al., Effects of Naturally Occurring Compounds on Fibril Formation and Oxidative Stress of $\beta$-Amyloid, Journal of Agricultural and Food Chemistry, 2005, vol. 53, pp. 8537-8541.

Suh, H., et al., Curcumin attenuates glutamate-induced HT22 cell death by suppressing MAP kinase signaling, Mol. Cell Biochem. (2007) vol. 298, pp. 187-194.

Pendurthi, U.R., et al., Inhibition of Tissue Factor Gene Activation in Cultured Endothelial Cells by Curcumin, Arteriosclerosis, Thrombosis, and Vascular Biology, 1997, vol. 17, 24 pgs.

Chan, M. et al., In Vivo Inhibition of Nitric Oxide Synthase Gene Expression by Curcumin, a Cancer Preventive Natural Product with Anti-Inflammatory Properties, Biochemical Pharmacology, 1998, vol. 55, pp. 1955-1962.

Kakar, S.S., et al., Curcumin inhibits TPA induced expression of c-*fos*, c-*jun* and c-*myc* proto-oncogenes messenger RNAs in mouse skin, Cancer Letters, vol. 87, 1994, pp. 85-89.

Singh, S., et al., Activation of Transcription Factor NF-κB is Suppressed by Curcumin (Diferulolylmethane), The Journal of Biological Chemistry, 1995, vol. 270, No. 42, pp. 24995-25000.

Egan, M.E., et al., Curcumin, a Major Constituent of Turmeric, Corrects Cystic Fibrosis Defects, Science, Apr. 2004, vol. 304, 11 pgs.

Kelloff, G.J., Chemopreventive Drug Development: Perspectives and Progress, Cancer Epidemiology, Biomarkers & Prevention, vol. 3, 1994, pp. 85-98.

Cappell, M.S., MD, PhD., et al., Diagnosis and Treatment of Nonsteroidal Anti-Inflammatory Drug-Associated Upper Gastrointestinal Toxicity, Gastroenterology Clinics, vol. 29, Issue 1, Mar. 2000, 13 pgs.

(56) References Cited

OTHER PUBLICATIONS

Christen, S., et al., γ-Tocopherol traps mutagenic electrophiles such as $NO_x$ and complements α-tocopherol: Physiological implications, Proc. Natl. Acad. Sci., USA, vol. 94, Apr. 1997, pp. 3217-3222.

Chan, M.M., et al., Effects of three dietary phytochemicals from tea, rosemary and turmeric on inflammation-induced nitrite production, Cancer Letters, vol. 96, 1995, pp. 23-29.

Bjørkman, D. MD, MSPH Nonsteroidal Anti-inflammatory Drug-Associated Toxicity of the Liver, Lower Gastrointestinal Tract, and Esophagus, The American Journal of Medicine, vol. 105 (5A), Nov. 1998, pp. 17S-21S.

Ireson, C.R., et al., Metabolism of the Cancer Chemopreventive Agent Curcumin in Human and Rat Intestine, Cancer Epidemiology, Biomarkers & Prevention, vol. 11, Jan. 2002, pp. 105-111.

Sugiyama, Y., et al., Involvement of the β-Diketone Moiety in the Antioxidative Mechanism of Tetrahydrocurcumin, Biochemical Pharmacology, vol. 52, 1996, pp. 519-525.

Pan, M., et al., Comparative Studies on the Suppression of Nitric Oxide Synthase by Curcumin and its Hydrogenated Metabolites through Down-regulation of IκB Kinase and NFκB Activation in Macrophages, Biochemical Pharmacology, vol. 60, 2000, pp. 1665-1676.

Okada, K., et al., Curcumin and Especially Tetrahydrocurcumin Ameliorate Oxidative Stress-Induced Renal Injury in Mice, The Journal of Nutrition, May 2001, pp. 2090-2095.

Weber, W., et al., TPA-induced up-regulation of activator protein-1 can be inhibited or enhanced by analogs of the natural product curcumin, Biochemical Pharmacology, vol. 72, 2006, pp. 928-940.

Kitani, K., et al., Interventions in Aging and Age-Associated Pathologies by Means of Nutritional Approaches, Ann. N.Y. Acad. Sci., vol. 1019, 2004, pp. 424-426.

Ravindranath, V., et al., Metabolism of Curcumin—Studies with [$^3$H] Curcumin, Toxicology, vol. 22, 1982, pp. 337-344.

Solima, K.F.A., et al., In vitro Attenuation of Nitric Oxide Production in C6 Astrocyte Cell Culture by Various Dietary Compounds, Food Constituents and NO Production, vol. 218, 1997, pp. 390-397.

Ammon, H.P.T., et al., Pharmacology of *Curcuma longa*, Planta Med., vol. 57, 1991, pp. 1-7.

International Search Report and Written Opinion dated Aug. 24, 2007 for corresponding PCT application No. PCT/US2007/05829.

Pan, et al. Biotransformation of Curcumin Through Reduction and Glucuronidation in Mice, Drug Metabolism and Disposition, 1999, vol. 27, 486-494.

\* cited by examiner

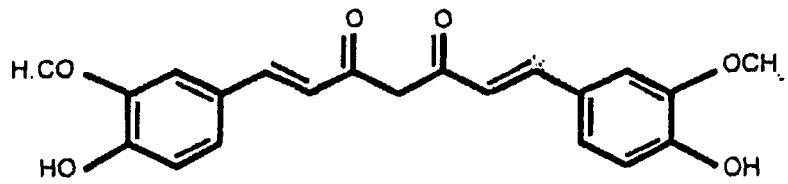
Curc
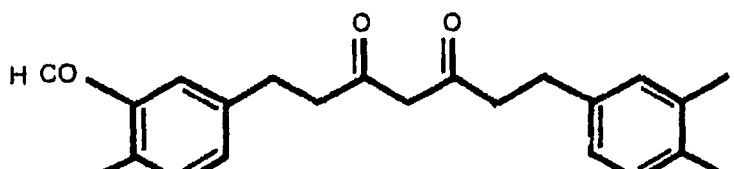
TC
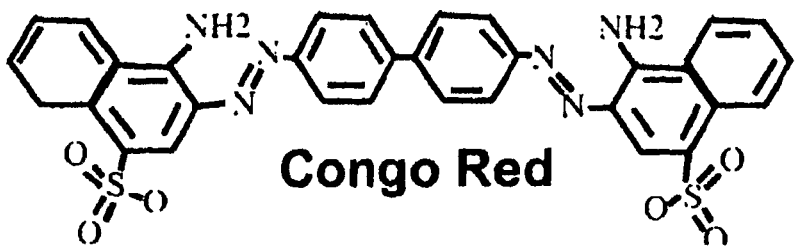
Congo Red
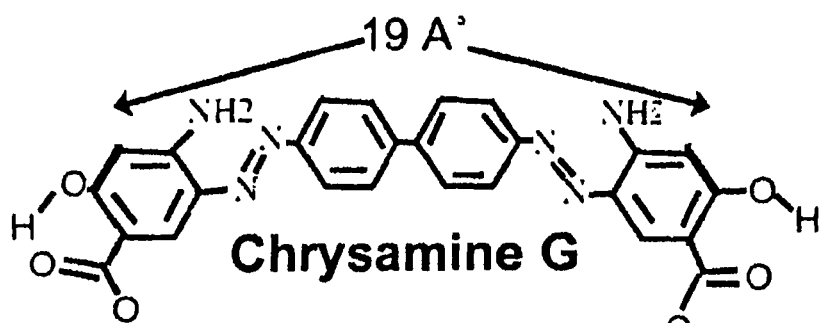
Chrysamine G
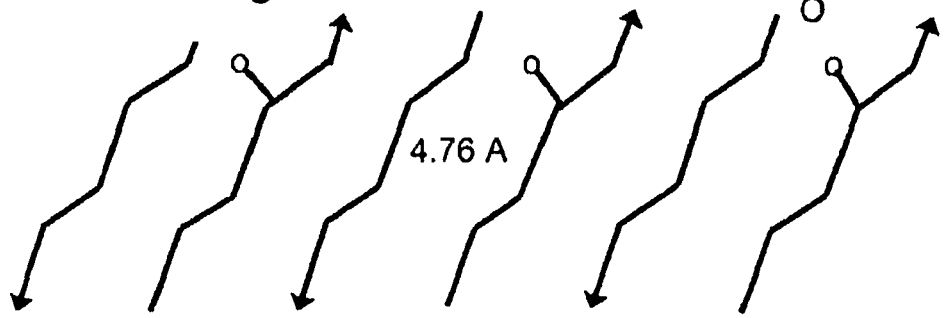
FIG 1

Figure 5
A
Acute dosing of Curc or TC
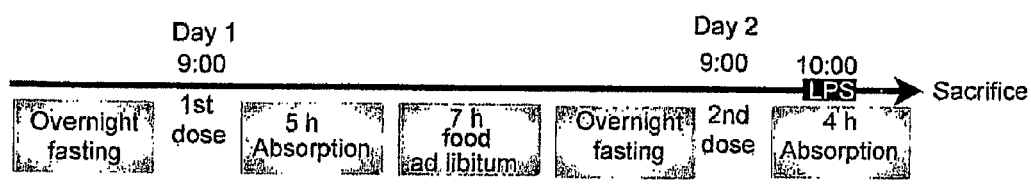
B
Chronic dosing of Curc or TC
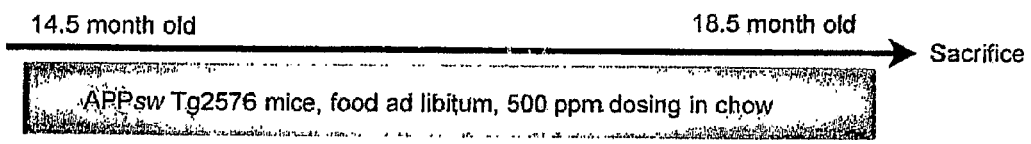

Figure 9
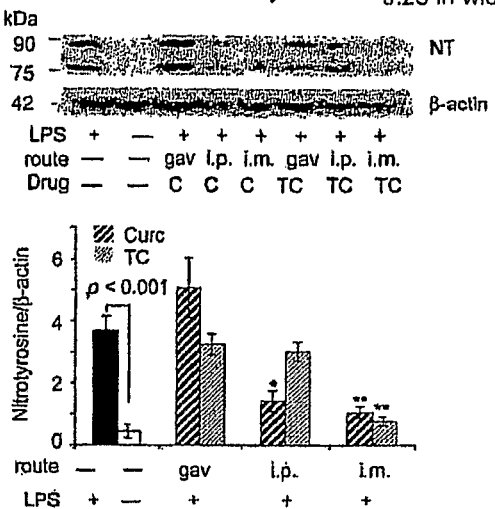
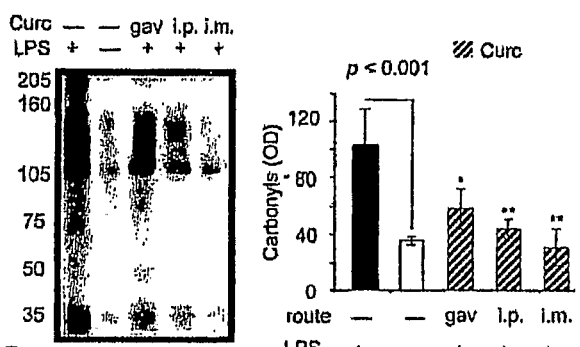
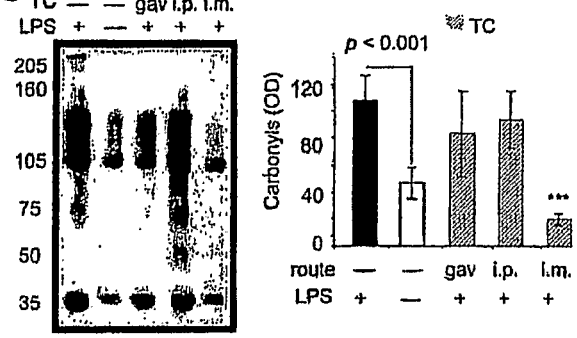

Figure 12
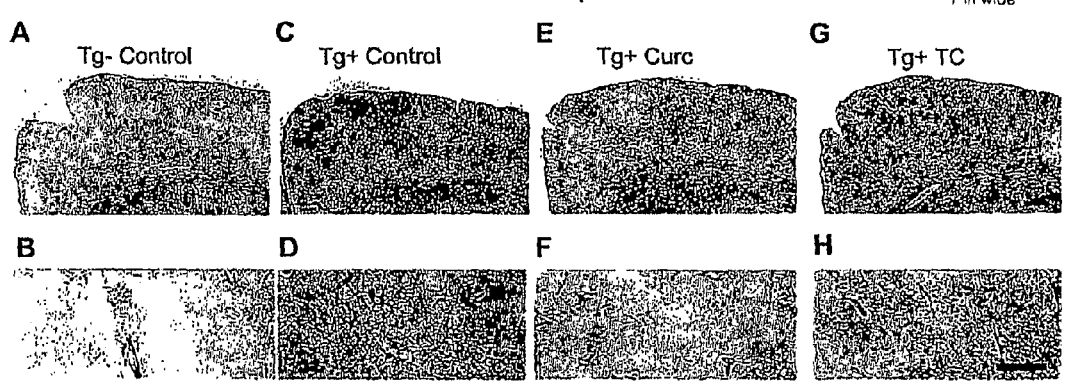
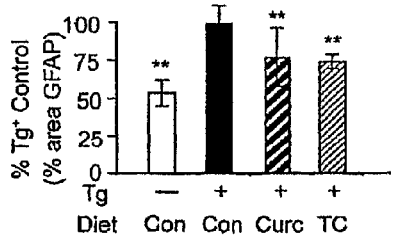

BIOAVAILABLE CURCUMINOID FORMULATIONS FOR TREATING ALZHEIMER'S DISEASE AND OTHER AGE-RELATED DISORDERS

CROSS-REFERENCE TO RELATED APPLICATION

This application is based on and claims priority to U.S. Provisional Patent Application No. 60/779,817, filed Mar. 6, 2006, the entire contents of which are incorporated herein.

STATEMENT REGARDING FEDERALLY SPONSORED RESEARCH OR DEVELOPMENT

This invention was made with Government support under Grant Nos. AG016750 and AG021975 awarded by the National Institutes of Health. The Government has certain rights in this invention. This work was supported by the U.S. Department of Veterans Affairs, and the Federal Government has certain rights in the invention.

FIELD OF THE INVENTION

The present invention generally relates to curcuminoid compositions useful in the treatment and prevention of disease, especially age-related diseases.

BACKGROUND OF THE INVENTION

Pathogenesis of diseases like Alzheimer's and Parkinson's show mounting evidence of oxidative damage and inflammatory factors. Unfortunately, despite strong epidemiology and rationale, antioxidant and NSAID approaches to these age-related diseases have generally not been successful in the clinic. For example, vitamin E has failed in trials for Alzheimer's and heart disease prevention, while COX inhibitors have failed for Alzheimer treatment and been dropped for prevention efforts with traditional antioxidants (selenium, vitamin E, β carotene), estrogens, and COX-2 inhibitors. The demographics of our aging population drive an urgent need for suitable alternatives for prevention and possible treatment of one or more of the chronic diseases of aging.

As a tumeric extract, curcumin is the yellow in yellow curries and is used as a food additive, for example, in yellow mustard. Like the "wonder drug" aspirin, which remains one of our few successful preventive agents, the long-term health potential of curcumin has a substantial history and a relatively well-established scientific basis. It has been identified as a major bioactive agent in an empirically developed system of traditional Indian and Chinese medicine.

Curcumin (diferulomethane) is not only a potent natural antioxidant and anti-inflammatory agent, acting on NFkB and AP-1 regulated pro-inflammatory mediators including COX-2, iNOS, il-1 and TNFα, but has multiple useful activities and has shown therapeutic potential in many pre-clinical culture and animal models for diseases, often related to aging. These include cancers (colon, prostate, breast, skin, leukemia, etc.) (Agarwal et al., 2003), prion disease (Caughey et al., 2003), atherosclerosis (Miquel et al., 2002; Ramaswami et al., 2004), stroke (G. Sun, personal comm.), CNS alcohol toxicity (Rajakrishnan et al., 1999), traumatic brain injury (F. Gomez-Pinilla, UCLA personal comm.), Huntington's disease (M F Chesselet, personal comm.), Marie-Charcot Tooth (J. Lupski, personal comm.), multiple sclerosis (EAE), and Alzheimer's disease.

Curcumin can block aggregation of Aβ and other amyloid-forming peptides to toxic fibrils and oligomers; chelate metals that cause lipid and protein and DNA oxidative damage to the brain; inhibit aberrant inflammation through AP-1 and NFkB transcription; stimulate beneficial microglial phagocytosis like the amylid vaccine to clear amyloid out of brain; and inhibit production of BACE under conditions of oxidative damage and inflammation, thus limiting Aβ production. Broad Spectrum efficacy for age-related disease is accentuated by positive life extension data (Kitani et al., 2004). Based on its outstanding safety profile and efficacy in multiple disease models with oxidative damage and inflammatory factors, curcumin has shown excellent potential for disease pathogenesis in Alzheimer models. Curcumin is on the short list of useful agents for cancer chemoprevention under development by the National Cancer Institute (NCI), which put curcumin through the National Toxicology Program and pre-clinical safety and efficacy trials (Kelloff et al., 1996; Chai-nani-Wu, 2003). Curcumin has passed several phase I trials for cancer and is currently in further clinical trials for cancers at multiple sites in the US and abroad.

Curcumin's structure resembles that of amyloid binding compounds. (FIG. 1) Amyloid dyes like Congo Red (CR) are known to bind via planar hydrophobic groups with appropriately spaced charge, and to suppress β-amyloid and other β-sheet-dependent peptide aggregation and toxicity. The Congo Red analogue, Chrysamine G, is more brain permeant and retains CR's amyloid binding properties. Curcumin shares the 19 angstrom CR spacing between its polar phenol groups; is readily brain permeant; and binds amyloid peptides, inhibiting their aggregation and toxicity in vitro. We have discovered that curcumin effectively reduces amyloid accumulation in vivo in APP Tg mice. Because CR's anti-amyloid binding is generic and potentially relevant to other β-sheet intraneuronal aggregates including Huntington, a-synuclein, prions and tau, curcumin's anti-amyloid activity may be relevant beyond extracellular amyloid to intraneuronal aggregates. In fact, curcumin is one of the most effective anti-prion compounds ever tested in vitro, although it did not work in vivo with oral dosing of unstated formulation (Caughey et al., 2003). This raises the limitations of curcumin oral bioavailability, the subject of the present invention.

The benefits of curcumin as a treatment for multiple diseases with aggregating amyloid proteins and other CAG repeat disorders are being established, and its efficacy in treating stroke, head trauma, metabolic syndrome, and many other conditions, including some forms of cancer and arthritis, as well as in promoting wound healing, is also beginning to be understood. All of these therapeutic applications are limited, however, because of poor intestinal absorption.

Although curcumin is an effective medication in multiple animal models for human diseases when given in chow at high doses (typically 2,000-5,000 ppm in diet in cancer trials), the current dogma is that it is so poorly bioavailable that it cannot be used for treatment outside the colon in humans. Curcumin is very hydrophobic and typically is not dissolved when delivered as a powder extract in common nutraceuticals. Most curcumin activities require 100-2,000 nanomolar (0.1-2 micromolar) levels in vitro, but current supplements result in negligible, low nanomolar blood levels (see Sharma et al., 2004). R. Sharma's group at Leicester has tried repeatedly and been unable to achieve significant blood levels beyond the low nanomolar range (Garcea G., Jones J D, Singh R., Dennison A R, Farmer P B, Sharma R A, Steward W P, Gescher A J, Berry D P. Detection of curcumin and its metabolites in hepatic tissue and portal blood of patients following oral administration. Br J Cancer. 2004 Mar. 8; 90

(5); 1011-5. PMID: 14997198.) They and others conclude that delivery of effective concentrations of oral curcumin to systemic tissues (outside the GI tract) is "probably not feasible." Most of the literature supports this view, leading the NCI to focus on colon cancer.

Three factors limit curcumin absorption and need to be addressed: 1) rapid glucuronidation/sulfation of curcumin's phenolic hydroxyl groups and high "first pass" clearance; 2) curcumin is unstable in aqueous solution at pH 7 and above; and 3) curcumin is very hydrophobic and typically is not water soluble at acidic pH and when delivered as a dry powder in existing supplements. (Most of the curcumin is never absorbed and simply passes through the GI tract and is excreted.)

Solubilization is critical to prevent this, but curcumin requires pH 8.5 to dissolve completely. For this reason, cancer patients are taking huge doses, typically up to 8 gms a day. Diarrhea is a common side-effect. Garcea, G. et al. (2004) report that with patients taking 3.6 gms of curcumin a day (as a standard powder extract capsule supplied by Sabinsa Corporation), blood and liver levels achieved are negligible. They conclude that "[t]he results suggest that doses of curcumin required to furnish hepatic levels sufficient to exert pharmacological activity are probably not feasible in humans."

Curcumin is not soluble at acidic pH and breaks down when solubilized and diluted into water at neutral or alkaline pH (e.g., in the GI tract, after the small intestine), due to keto-enol transformations in the β-diketone bridge. In addition, curcumin is susceptible to rapid glucuronidation/sulfation The major U.S. supplier, Sabinsa, has tried to make a more bioavailable form by adding Bioperine (piperine) to inhibit glucuronidation. Such an approach is flawed, however, because most glucuronidation takes place in the upper GI tract, where the pH is acidic, and curcumin is not completely dissolved until pH 8.5 and higher. Even worse, inhibiting glucuronidation can cause serious health risks. Glucuronidation is protective against many toxins and involved in the metabolism of commonly used drugs. Most elderly patients are on multiple drugs, at levels likely to be unsafely altered by inhibition of glucuronidation.

Although many groups have come up with theoretical ideas for improving absorption of curcumin, most have involved entirely in vitro studies, probably because of the difficulty in measuring curcumin and its metabolites in tissue. Our facilities, knowledge, and experience in measuring curcumin and tetrahydrocurcumin have yielded a better approach.

SUMMARY OF THE INVENTION

The present invention provides curcuminoid compositions that exhibit enhanced bioavailability and can be used as therapeutic agents to treat, and possibly slow or prevent, a number of aged-related diseases and conditions. In one aspect of the invention, a curcuminoid composition having enhanced bioavailability comprises a curcuminoid, an antioxidant, and a water-solubilizing, pharmaceutically acceptable carrier, and optionally a glucuronidation inhibitor. In one embodiment, solubilization is achieved by forming curcuminoid-lipid micelles, and the composition is provided as a microemulsion or solid lipid nanoparticles (SLN). In another embodiment, the curcuminoid is dissolved in an edible oil, which can then be microencapsulated or emulsified. The composition can be provided as a gel, capsule, liquid, or other pharmaceutically acceptable form.

The invention also provides a method of treating, slowing, and/or preventing disease, particularly neurodegenerative age-related diseases such as Alzheimer's, and comprises administering a therapeutically effective dose of a solubilized, hydrolysis-resistant, optionally glucuronidation-resistant, curcuminoid. Functional curcuminoid doses can be provided in mammals, such as rats, mice, and humans, using an improved curcuminoid composition as described herein.

BRIEF DESCRIPTION OF THE DRAWINGS

These and other features and advantages of the invention will become better understood when considered in conjunction with the following detailed description and by making reference to the appended drawings, wherein:

FIG. 1 depicts the molecular structures and similarity of molecular spacing of Congo Red, Curcumin, and Chrysamine G;

FIG. 5 shows two diagrams of acute and chronic dosing of curcumin (Curc) or tetrahydrocurcumin (TC), according to embodiments of the present invention;

FIG. 9 shows quantification of brain nitrotyrosine (NT) and carbonyls in mouse brain homogenates in mice treated with Curc or TC as indicated, according to embodiments of the present invention;

FIG. 12 shows micrographs and quantification of Tg2576 (Tg+) and control (Tg−) mouse brains stained for glial fibrillary acidic protein (GFAP) from mice given a Curc, TC, or control (Con) diet, according to embodiments of the present invention;

DETAILED DESCRIPTION OF THE INVENTION

Figure 2:
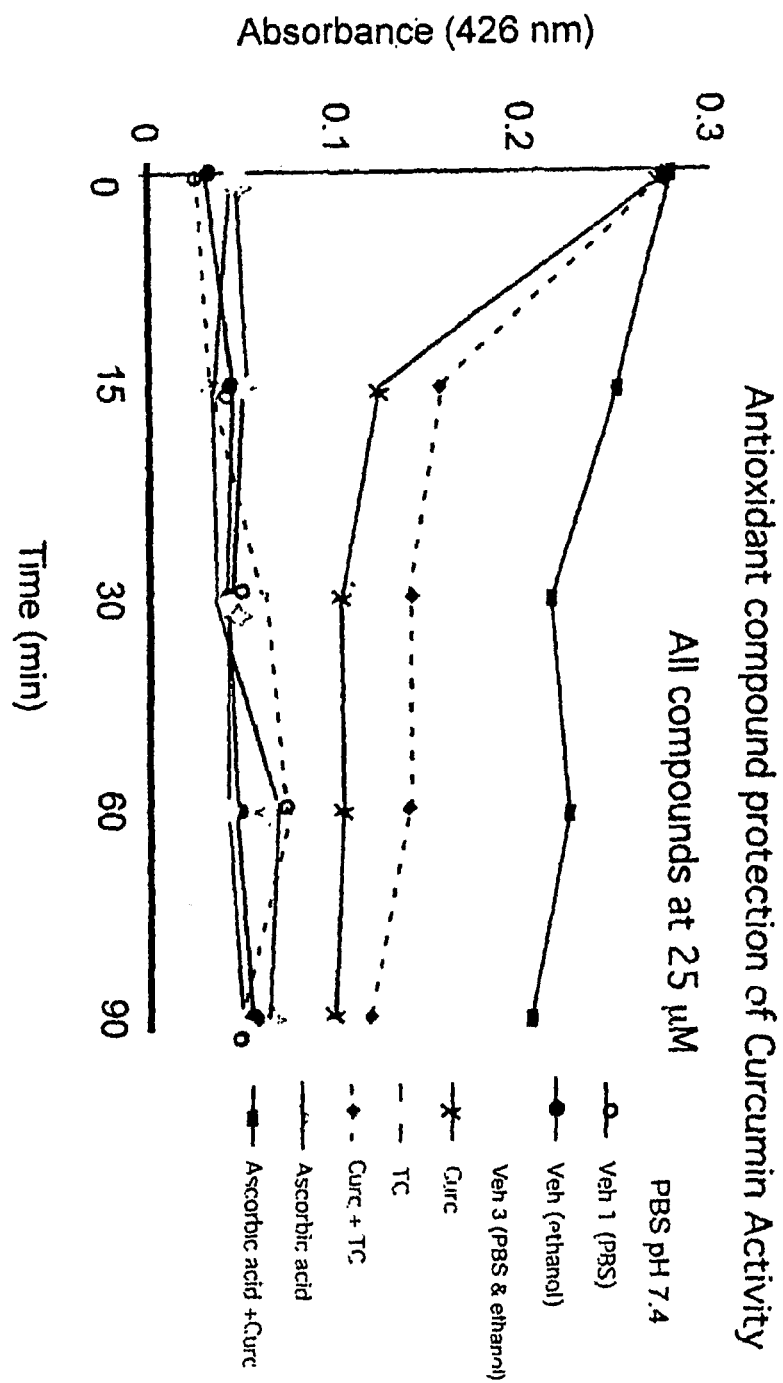
FIG. 2 is a graph of absorbance vs. time for antioxidant protection (stabilization) activity of various formulations of curcumin, tetrahydrocurcumin, and ascorbate.

The present invention provides curcuminoid compositions that exhibit enhanced bioavailability. In one aspect, such a composition comprises a curcuminoid, an antioxidant (which stabilizes the curcuminoid against hydrolysis), a water-solubilizing, pharmaceutically acceptable carrier, and, optimally, a glucuronidation inhibitor. In some embodiments, for example where the curcuminoid is tetrahydrocurcumin, which is stable even at alkaline pH, the antioxidant may be dispensed with. In various embodiments, the composition is provided as a microemulsion, solid lipid nanoparticles (SLN), microencapsulated oil, gel, capsule, liquid, and/or other pharmaceutically acceptable form, and is suitable for administration to a human or other mammal enterally, parenterally, topically, or by some other mode of administration.

Nonlimiting examples of curcuminoids include curcumin, tetrahydrocurcumin, demethoxycurcumin, bisdemethoxycurcumin, curcumin esters (which function as prodrugs), and mixtures thereof. The combination of curcumin and its metabolite, tetrahydrocurcumin, is particularly effective. Tetrahydrocurcumin is relatively stable in water at physiologic pH, is a competitive inhibitor of glucuronidation, and enhances absorption and, ultimately, plasma levels of curcumin.

To protect the curcuminoid against hydrolysis, a water-soluble antioxidant is employed. Nonlimiting examples include ascorbic acid (ascorbate, vitamin C and its acylated fat soluble derivatives), α-lipoic acid (alpha-lipoate), vitamin E and derivatives, N-acetylcysteine (NAC), and reduced glutathione (GSH). Even tetrahydrocurcumin provides curcumin some protection against hydrolysis. Mixtures of antioxidants also can be used.

Most previous efforts to explain curcumin's poor bioavailability have focused on rapid glucuronidation. However, tetrahydrocurcumin and curcumin are similarly hydrophobic and poorly soluble in water, and similarly rapidly glucuronidated and sulfated. Nevertheless, our data and data in the literature show that tetrahydrocurcumin is much more bioavailable than curcumin, with plasma levels from the same oral doses that are 7-8 times higher. The improved bioavailability of tetrahydrocurcumin is largely attributed to the fact that it is stable even at basic pH. In contrast, curcumin is unstable in aqueous solutions above pH 7.0 and therefore unstable in the intestinal tract where most absorption occurs. It hydrolyzes to ferulic acid and vanillin breakdown products. A preparation that stabilizes curcumin at slightly more basic pH is predicted to increase bioavailability of solubilized curcumin by as much as 7-8 fold. Combining curcumin with an additional water soluble antioxidant, for example ascorbate, can stabilize curcumin at pH 7.4.

We have tested serial dilutions of ascorbate and find stabilization is effective out to 4 hours (a typical absorption cycle), with curcumin:ascorbate ratios as high as 16:1, with some small decline in efficacy between 8:1 and 16:1. Therefore, providing a curcuminoid-to-antioxidant ratio of about 10:1 or higher should be sufficient to prevent hydrolysis during absorption, and enhance bioavailability. As one nonlimiting example, a preparation containing 330 mg of curcumin (MW 368) would have only an additional 17.75 mg of ascorbate (MW 198). Thus, additional antioxidant need not add prohibitively to the bulk of a formulation.

Nonlimiting examples of glucuronidation inhibitors include tetrahydrocurcumin, piperine (Bioperine®), probenecid (Probene®), and diclofenac. (See e.g., Uchaipichat V, Mackenzie P I, Guo X H, Gardner-Stephen D, Galetin A, Houston J B, Miners J O. Human udp-glucuronosyltransferases: isoform selectivity and kinetics of 4-methylumbelliferone and 1-naphthol glucuronidation, effects of organic solvents, and inhibition by diclofenac and probenecid. Drug Metab Dispos. 2004 April; 32 (4):413-23; Vree T B, van den Biggelaar-Martea M, Verwey-van Wissen C P, van Ewijk-Beneken Kolmer E W. Probenecid inhibits the glucuronidation of indomethacin and O-desmethylindomethacin in humans. A pilot experiment. Pharm World Sci. 1994 Feb. 18; 16 (1):22-6.) Mixtures of inhibitors can also be used. Curcumin and tetrahydrocurcumin are rapidly removed by high first-pass glucuronidation, and inhibition of glucuronidation with piperine is reported to improve curcumin bioavailability in humans. However, addition of a glucuronidation inhibitor raises issues of interactions with the many other drugs eliminated by glucuronidation. The present invention can improve bioavailability without such an inhibitor, but it is included as an optional component in some formulations.

Despite its poor bioavailability, oral dosing with curcumin in vivo can competitively and transiently inhibit glucuronidation of other drugs, for example, mycophenolic acid. (Basu et al Nikhil K. Basu, Labanyamoy Kole, Shigeki Kubota, and Ida S. Owens, Human UDP-Glucuronosyltransferases Show Atypical Metabolism of Mycophenolic Acid and Inhibition by Curcumin. Drug Metabolism and Disposition 32:768-773, 2004). Tetrahydrocurcumin, which gives 7-8 times higher levels, is predicted to be much more available, more stable, and therefore, more effective than curcumin, and tetrahydrocurcumin is predicted to protect curcumin from glucuronidation. Further, our in vitro bioassay data show that, at 1:1 ratios, tetrahydrocurcumin and curcumin synergize together in vitro. Therefore, formulating tetrahydrocurcumin with curcumin with 1:1 or higher molar ratios of tetrahydrocurcumin to curcumin will improve bioavailability of curcumin and provide synergistic efficacy.

Glucuronidation and sulfation of curcuminoids can also be inhibited by esterifying a fatty acid or other acyl group to one or both hydroxyls in the two methoxyphenol groups that are the targets of rapid enzymatic glucuronidation and sulfation. The blocking ester groups will then be removed from the prodrug curcuminoid ester in vivo by esterases in the target tissues, releasing free curcumin. In principle, any fatty acid can be used for esterification. Because our data show effective in vivo synergism between the omega-3 fatty acid docosahexaenoic acid (DHA) and curcumin in an Alzheimer model, DHA is an attractive choice. Not only is DHA selectively taken up by the brain, where curcumin is neuroprotective in multiple systems, but DHA can also target drugs to tumor cells, a major clinically relevant target of curcumin. (For DHA-targeting of lipophilic cancer drugs to tumor cells see Bradley M O, Swindell C S, Anthony F H, Witman P A, Devanesan P, Webb N L, Baker S D, Wolff A C, Donehower R C, Tumor targeting by conjugation of DHA to paclitaxel. J Control Release. 2001 Jul. 6; 74 (1-3):233-6; Harries M, O'Donnell A, Scurr M, Reade S, Cole C, Judson I, Greystoke A, Twelves C, Kaye S; Phase I/II study of DHA-paclitaxel in combination with carboplatin in patients with advanced malignant solid tumors. Br J Cancer. 2004 Nov. 1; 91 (9): 1651-5.) Further, long chain polyunsaturated fatty acids like DHA increase drug targeting to the lymphatics which reduces first pass metabolism issues.

Thus, a "prodrug" DHA-curcuminoid can be synthesized from a curcuminoid (e.g., curcumin) and DHA by coupling DHA to curcumin at a phenolic hydroxyl with 1:1 stoichiometry, analogous to Bradley et al 2001 for paclitaxel. (Bradley M O, Webb N L, Anthony F H, Devanesan P, Witman P A, Hemamalini S, Chander M C, Baker S D, He L, Horwitz S B, Swindell C S. Tumor targeting by covalent conjugation of a natural fatty acid to paclitaxel. Clin Cancer Res. 2001 October; 7 (10):3229-38.) Alternatively, DHA can be coupled to curcumin by a multi-step scheme analogous to that used to couple doxorubicin to curcumin (Wang Y, Li L, Jiang W, Yang Z, Zhang Z. Synthesis and preliminary antitumor activity evaluation of a DHA and doxorubicin conjugate. Bioorg Med Chem Lett. 2006 Jun. 1; 16 (11):2974-7.) DHA-curcumin esters will deliver neuroprotective DHA and neuroprotective curcumin with longer half-life and improved bioavailability.

More generally, a curcuminoid ester according to one aspect of the invention can comprise the esterification product of a curcuminoid and a carboxylic acid RCOOH, where R is selected so that the resulting ester is non-toxic and subject to cleavage by an esterase in vivo. A preferred class of carboxylic acids for this purpose is fatty acids, especially essential fatty acids, such as DHA (an omega-3 fatty acid). Mono-, di- and triglycerides are additional examples of carboxylic acids suitable for making curcuminoid prodrugs.

The curcuminoid is solubilized using any of a number of water-solubilizing carriers. As used herein, "water-solubilizing carrier" refers to an agent, composition, compound, or medium that provides a curcuminoid in a more water-soluble or water-dispersible form, or that interacts with the curcuminoid to impart greater water solubility or dispersibility. Broadly, two nonlimiting categories of carriers include lipid micelles and microencapsulated oils.

Lipids micelles containing a curcuminoid can be made with any of a variety of lipids. Nonlimiting examples include (i) fatty acids, e.g., stearic acid; (ii) phospholipids, for example, phosphoglycerides, e.g., phosphatidyl choline ("PC"), phosphatidylethanolamine, phosphatidylinositol; (iii) bile acids, e.g., deoxycholic acid (deoxycholate) and conjugates thereof (e.g., amino acid conjugates, such as glycocholate and taurocholate); (iv) edible oils, especially healthful oils, e.g., vegetable oils, olive oil, canola oil, fish oil; (iv triacylglycerols; (vi) mixtures of any of these and/or other lipids and derivatives, e.g., pharmaceutically acceptable salts, hydrates, and conjugates thereof. The combination of a phospholipid (e.g., PC or Soy lecithin or Egg lecithin) and another surfactant—such as bile acid/salt (e.g., deoxycholate, taurocholate), Ethylene oxide/propylene oxide copolymers (Poloxamer 188, Polosamer 182, Poloxamer 407, Poloxamine 908), or Sorbitan ethylene oxide/propylene oxide copolymers (Polysorbate 20, Polysorbate a60, Polysorbate 80)) is particularly useful. Other useful lipids include natural lecithin, (a mixture of glycolipids, triglycerides, and phospholipids, including PC). In general, longer chain compounds are preferred over short chain compounds when the composition is provided as an emulsion.

In one embodiment, micelles are prepared using a protocol modified from Began et al 1999. (Began G, Sudharshan E, Udaya Sankar K, Appu Rao A G. Interaction of curcumin with phosphatidylcholine: A spectrofluorometric study. J Agric Food Chem. 1999 December; 47 (12):4992-7.) Thus, PC-Curcumin micelles can be prepared using a mixture of phosphatidylcholine (PC) and deoxycholate (DOC), at a DOC:PC molar ratio of 2.0. Curcumin (10 mg) is added to the DOC/PC mixture, solubilized together in a chloroform/methanol (2:1 by volume) mixture. The mixture is then evaporated and dried with nitrogen. The resulting thin film is resuspended in 2 ml of phosphate buffered saline (PBS), pH 7.4, and then the solution (5 mg/ml) is sonicated for 5 min using a bath sonicator.

Began et al performed all experiments in vitro and used a 2:1 molar ratio of DOC:PC, and found that micelles were saturated with curcumin at a 6 or 7:1 molar ratio of PC to curcumin. In contrast, in one embodiment of the invention, micelles are formed with a DOC:PC molar ratio of 3.7:1 and a molar ratio of PC to curcumin of 1:3.33 (see Ex. 1). In general, surfactant-to-lipid ratios (e.g., DOC-to-PC ratios) of 1:1 to 4:1 are used. Bioavailability may theoretically be further improved by increasing the PC:curcumin ratio, up to a saturating 6:1 ratio, but the bulk PC will reduce the amount of curcumin achievable per 1 g capsule.

In some embodiments the micelles also contain either or both of the antioxidant and the glucuronidation inhibitor. Alternatively, the latter two components are added to the composition after micelle formation. In either case, the micelles can be administered in a variety of clinically deployable forms (e.g., diluted in saline and administered as a liquid; compounded with a binder and other excipients, and administered as a capsule; etc.).

It is also possible to form lipid micelles in vivo by, e.g., dissolving a curcuminoid in an ingestible oil, adding an antioxidant and glucuronidation inhibitor; microencapsulating the combined components, and allowing bile acids to form micelles in vivo.

The second broad category of "water-solubilizing carriers" is microencapsulated oils, in which microdroplets of a non-toxic oil, preferably an edible oil, especially healthful oils (e.g., vegetable oils, olive oil, canola oil, and fish oils) are surrounded by a coating, shell, or other membrane that is water-soluble or decomposes in water. Microencapsulated oils are known in the pharmaceutical field and can be prepared by a number of methods, including air-suspension coating, centrifugal extrusion, vibrational nozzle, and spray-drying. In one embodiment, the coating dissolves or breaks down in the GI tract with zero-order or first-order kinetics. The microencapsulated oils can be administered orally (with e.g., formulation as desired to provide a capsule or other delivery system), or by another suitable mode of administration. Particles can be stabilized with polysorbate 80 (e.g.,) standard gel caps or chitosan-coated gel caps can also be used to hold the formulations and promote intestinal delivery.

In another embodiment of the invention, the composition is provided as solid lipid nanoparticles (SLNs), which can be administered in a variety of clinical forms, for example, in gels caps, or by formulation with one or more binders or other excipients. The preparation of SLNs is known in the art. See, e.g., Luo, Y., Ren, L., Zhao, X., Qin, J., Solid Lipid Nanoparticles For Enhancing Vinpocetine's Oral Bioavailability, J. Controlled Release, 114 (2006) 53-59 (available online at www.sciencedirect.com and incorporated herein by this reference).

Nonlimiting examples of suitable lipids for SLNs include: triacylglycerols, e.g., tricaprin, trilaurin, trimyristin, tripalmitin, tristearin; acylglycerols, e.g., glycerol monostearate, glycerol behenate, glycerol palmitostearate; fatty acids, e.g., stearic acid, palmitic acid, decanoic acid, behenic acid; waxes, e.g. cetyl palmitate; cyclic complexes, e.g., cyclodextrin, para-acyl-calix-arenes; and mixtures thereof.

Nonlimiting examples of suitable surfactants include: Phospholipids, e.g., soy lecithin, egg lecithin, phosphatidylcholine; ethylene oxide/propylene oxide copolymers, e.g., Poloxamer 188, Poloxamer 182, Poloxamer 407, Poloxamine 908; sorbitan ethylene oxide/propylene oxide copolymers, e.g., Polysorbate 20, Polysorbate 60, Polysorbate 80; alkylaryl polyether alcohol polymers, e.g., tyloxapol.

Nonlimiting examples of suitable co-surfactants include: Sodium cholate, sodium glycocholate, sodium taurocholate, sodium taurodeoxycholate.

There are many ways to prepare SLN formulations. As but one general example, one can use hot homogenation in which a lipid is heated to about 10 degrees over its melting temperature; a lipophilic drug is added and dissolved in the lipid; surfactant is added at a 1:1 to 2:1 surfactant-to-lipid ratio; and the combination is cooled and then dispersed by sonication (typical particle size: 100 mm). Such a method scales up easily. (In contrast, evaporation methods are harder to scale up.) In general, for surfactants such as lecithin, deoxycholate, taurocholate, or commercial surfactants such as Tureen 80 and polyoxyethylene hydrogenated castor oil (Cremaphor), increasing the surfactant-to-lipid ratio to 1.5, 1.75, or even 2:1 tends to reduce the particle size and improve absorption. Natural surfactants are preferred, at least in part, because curcumin is typically marketed as a neutraceutical, and there is a perception that "natural" is safer.

Efficacy.

In vivo data acquired by administering to mice curcumin freshly dissolved in base (0.5M NaOH) and rapidly diluted into neutralizing PBS (where it is unstable) and delivered immediately via gavage or by i.p. or i.m. showed that plasma levels in the 0.25-0.5 micromolar range gave brain levels sufficient to give IC50's for ~50% inhibition of pro-inflammatory IL-1β, iNOS and a cell death-related MAP kinase (active c-jun kinase (p)JNK).

For comparison, on a drug wt/kG body weight basis, which generally exaggerates human doses, this is 1 mg/30 g=33.3 mg/kG and translates to ~2.5 gms per 75 kG person, which is well within the range given to patients in clinical trials.

Thus, one example of a practical formulation combining all 3 principles (solubilization with lipid, protection with antioxidant, and competitive inhibition and synergy with tetrahydrocurcumin), for humans would be 165 mg curcumin, 165 mg tetrahydrocurcumin, 17.7 mg of stabilizing antioxidant (ascorbate, lipoate, NAC, GSH etc) and the rest DOC/PC micelles as above or as other amphiphilic lipids, for a 1 gm capsule. Binders, processing aids, and other excipients can also be present.

The following are selected curcuminoid formulations that can be prepared according to the present invention.

Formula 1. PC-DHA Curcumin/Tetrahydrocurcumin Micelles

Curcumin, tetrahydrocurcumin (enhances absorption, synergizes with curcumin), phosphatidylcholine (emulsifies, makes micelles with deoxycholate salt, greatly enhances absorption), docosahexaenoic acid (from marine oil; synergizes with curcumin, facilitates curcumin delivery to brain or tumors), an antioxidant or antioxidant mix (vitamin C or lipodated vitamin C, alpha-lipoic acid, vitamin E) (used to stabilize and recycle curcumin, maintaining its stability and preventing it from becoming a pro-oxidant in the capsule or in the body).

Formula 2. PC-DHA Curcumin Micelle

Curcumin (we have determined that 25% of curcuminoids in plasma are naturally converted to tetrahydrocurcumin which enhances absorption, synergizes with curcumin), phosphatidylcholine, docosahexaenoic acid, an antioxidant or antioxidant mix (vitamin C or lipodated vitamin C, alpha-lipoic acid, vitamin E)

Formula 3. Olive Oil/DHA Curcumin

Curcumin, docosahexaenoic acid, an antioxidant or antioxidant mix (vitamin C or lipodated vitamin C, alpha lipoic acid, vitamin E). Our data shows that when curcumin is dissolved in oil, plasma curcumin remains low, but red blood cell curcumin is quite high, which explains bioavailability despite negligible plasma levels. No other group has reported this fundamental observation that appears to be the simplest method of enhancing bioavailability. Other healthful oils can be used (fish oil, canola oil, other high omega-3 oil). In this formulation, curcumin in oil can be microencapsulated.

Formula 4. DHA-Curcumin Ester

Prodrug. A novel compound that resolves problems with curcumin bioavailability and efficacy in humans that has optimal oral absorption, antioxidant activities in the brain, anti-amyloidogenic properties (e.g., DHA reduces amyloid production and accumulation), resistance to glucuronidation. Can be compounded as a micelle, SLN, or other formulation.

Formula 5. DHA-Curcumin Ester and DHA-Tetrahydrocurcumin Ester

Another Prodrug with enhanced oral availability and stability.

Formula 6: Curcumin-SLN

Using high melting point fats, solubilized, hydrolysis-resistant curcuminoid formulations can be made into clinically deployable solid lipid nanoparticles (SLN) made with an internal phase lipid a drug (curcuminoid), a surfactant, and a co-surfactant.

In addition to the compositions provided herein, the invention also provide a method of treating various diseases, particularly neurodegenerative, age-related diseases, such as Alzheimer's disease. In one embodiment, the method comprises administering to a mouse, rat, human, or other mammal a therapeutically effective dose of a curcuminoid, wherein the curcuminoid is provided as a composition as described herein, e.g., as lipid micelles, microencapsulated oils, SLN, etc., optionally as a gel, capsule or liquid. For humans, most curcumin activities require 100-2,000 nanomolar (0.1-2 micromolar) levels in vitro.

Inclusion of a solubilizing lipid greatly enhances the plasma and red blood cell levels of curcumin. In one experiment, 1:1 DHA:lecithin micelles were prepared, putting curcumin in hot DHA (55° C.) and sonicating to disperse Curcumin delivered by PC-DHA micelles (but without an antioxidant or separate glurondation inhibitor), and a curcumin concentration of 0.29 Mg/ml plasma and 0.96 in red blood cells was achieved (0.8 and 2.6 mm respectively). In contrast, using the Sabinsa formulation (with piperine, but no water-solubilizing carrier) yielded a curcumin concentration of 0.17 Mg/ml in plasma (0.46 mm). Long chain fatty acids, particularly unsaturated ones like DHA, have added value in routing lopohilic drugs to the lymphatics and reducing high first-pass losses.

EXAMPLES

The following are nonlimiting examples of the invention, its preparation, and its use in vivo.

Materials

Stearic acid, L-phosphatidylcholine (lecithin), sodium taurocholate, deoxycholate, and doubly distilled (dd) nanopure water are from Sigma. DHA and curcumin (97%) are from Cayman Chemicals (Michigan, Mich.). Tetrahydrocurcumin (99%) is from Sabinsa Corporation (Piscataway, N.J.).

General Nanoparticle Protocol—Hot Homogenization (Modified From Bocca et al., 1998)

1. Set water bath to ~75-80° C. to melt lipid.
2. Measure lipids, surfactants, and water per test formula and batch size.

3. Add internal phase lipid (stearic acid or DHA) and drug and lecithin (surfactant) with magnetic stirring to empty jacketed vessel.
4. Add sodium taurocholate (co-surfactant) to water, continuing stirring.
5. Heat dd water solution to 75° C. on heated plate
6. Once lipid has melted, add water solution to jacketed vessel.
7. Allow combined lipid-water solution to equilibrate at 75° C.
8. Disperse solution in an Ika Ultra-Turrax T 18 rotor-stator homogenizer (with 19 mm rotor stator) at 30,000 rpm for 2 minutes.
9. Rapidly inject/disperse 1 ml of warm micro-emulsion via small gauge needle into 10-20 ml of 2° C. dd water in glass vial with continuous stirring.
10. Wash 3× in dd water by diafiltration using a TCF2 apparatus with a YM100 kD cut off membrane (Amicon, Danvers, Mass.).
11. Store lipid nanoparticle product at 2° C.
12. Measure particle size.

Optimization.

In order to achieve a target of 100 nm size for parenteral administration and a target polydispersity of 0.10, stearic acid has generally been selected as the lipid to use. However, for oral delivery, larger size particles may be acceptable. Absolute amounts depend upon batch sizes, but appropriate stoichiometry is known from the literature. Using this protocol a lecithin (phosphatidylcholine) to sodium taurocholate ratio of 2.3, a surfactant to lipid ratio of 1.4, and a mixing time of 70 seconds with a mixing speed of 18,000 RPM have been found to be optimal for beta carotene which gave a mean entrapment efficiency of 40% and a concentration of 0.22 mg/ml (Triplett, 2004).

Solid Lipid Nanoparticles (SLN) Preparation

Starting Formula.

Stearic Acid mole fraction 0.710; lecithin mole fraction 0.210; taurocholate mole fraction 0.069; curcumin or other curcuminoid varies stepwise around mole fraction 0.011. Stearic acid lipid is maintained at ~75° C. to melt completely. Separately, double distilled water is heated to 75° C. Typically, surfactants are added to the water under magnetic stirring and allowed to equilibrate at 75° C. The water-surfactant solution is added to the melted lipid and allowed to equilibrate at 75° C. The IKA Ultra-Turrax T 18 rotor-stator homogenizer is then used to achieve adequate mixing, typically 18,000-30,000 rpm for 70-150 sec. Once mixed, the dispersed lipid phase of the emulsion is solidified in order to produce the solid lipid nanoparticles by dispersing through a narrow gauge needle 1 ml emulsion aliquots into continuously stirred near ice cold water (~2° C.) at a ratio of 1:20 (warm micro-emulsion: cold water). The final product is washed three times with distilled water and filter sterilized with an Amicon Diaflo apparatus with YM100 membranes (cut off 100 000 Dalton) and stored sterile at 4° C. until delivery by gavage. Multiple lipid nanoparticle samples can be prepared from one micro-emulsion batch.

Determine Efficiency of Incorporated Drug:

To determine the amount of the incorporated drug, the SLN dispersions (or micelles) are freeze-dried using a freeze-dryer. Unloaded SLN for each formulation, i.e. SLN not carrying either drug, is also prepared as described above. The amount of curcumin incorporated into SLN can then be determined by dissolving freeze-dried SLN in 95% ethyl acetate/5% methanol, evaporating it under $N_2$ gas and then resuspending the sample by mobile phase C reagent (41% acetonitrile, 35% de-ionized water, 23% methanol and 1% acetic acid; v/v/v/v). This sample is analyzed by isocratic HPLC methods with a reversed-phase C18 column (3.9×150 mm, 5-É m particle size; Waters Corporation, Massachusetts, MA) using ultraviolet (UV) detection at a wavelength of 262 nm (Heath et al., 2003; Heath et al., 2005).

Drug Loading and Release Measurements.

UV-Visible photospectroscopy (UV-Vis) is employed to measure drug loading of lyophilized samples using ethanol as the solvent to dissolve the dried lipid nanoparticles or micelles and eliminate secondary scattering and absorption errors. All absorption readings are conducted at a wavelength at which curcumin (262 nm-UV 426 nm-visible) or a curcuminoid (XnM) absorbs most strongly relative to the other light absorbing molecules used in these studies. Other molecules with detectable absorbance include sodium taurocholate and lecithin which can be corrected for assuming a linear relationship between absorbance and concentration and with a calibration curve for each absorbing molecule. These are provided by no-drug SLN or micelle controls as "blanks." Given known concentrations of all components except curcumin or derivatives, the drug concentration can be calculated from the corrected absorbance. Stability is assessed after different storage methods and times for micelle preparations.

Characterization of Nanoparticle Diameters.

Atomic Force Microscopy

Atomic force microscopy (AFM) can be used to obtain images of lipid nanoparticles preparation sizes. Small quantities of lipid nanoparticle suspension are placed on the substrate and allowed to air dry before imaging, realizing that this may flatten the particles during drying, resulting in slightly larger particle sizes than obtained with dynamic light scattering methods.

Example 1

DOC/PC/Curcumin Micelles and Gavage Administration to Mice

To make 5 mg of curcumin micelles having a DOC:PC molar ratio of 3.7:1 and a molar ratio of PC to curcumin of 1:3.33, to orally dose 5 mice at 1 mg per ~30 gm mouse, we mix 12.438 mg DOC to 6.219 mg PC (mass ratio 2:1) and 10 mg curcumin powder. This was dissolved by vortexing in 2 ml of chloroform/methanol (2:1) mixture. The solvent was evaporated and dried under nitrogen. The resulting emulsion film was scraped into 2 ml of phosphate buffered saline (PBS), pH 7.4, and sonicated in a bath sonicator for 5 minutes, and 1 mg (200 μL) was administered by gavage per mouse to produce a plasma concentration of 0.465 micromolar, which was more than double the plasma level without micelles The dry mass of the preparation was 2.865 mg/mg curcumin or curcuminoids which would permit ~350 mg of curcumin per 1 gm capsule or 175 mg/500 mg capsule, practical amounts.

Example 2

DHA-Curcuminoid Ester

A curcuminoid ester can be synthesized from curcumin and DHA by coupling DHA to curcumin at a phenolic hydroxyl with 1:1 stoichiometry, analogous to Bradley et al 2001 for pacliataxel. To a solution of curcumin (366 mg; 1 mol) in methylene chloride (61 ml) under argon, one adds 4-dimethylaminopyridine (122 mg; 1 mol), 1,3-dicyclohexylcarbodiimide (412.36 mg; 2 mol), and DHA (329.4 mg; 1 mol). The reaction mixture is stirred at room temperature for 2 h. After dilution with diethyl ether, the reaction mixture is washed with 5% HCl, water, and saturated aqueous NaCl. The mixture is dried with sodium sulfate and concentrated and chromatographically purified. DHA-curcumin is then used as curcumin would be, e.g., in mixed micelle or gel formulations. (See Bradley M O, Webb N L, Anthony F H, Devanesan P, Witman P A, Hemamalini S, Chander M C, Baker S D, He L, Horwitz S B, Swindell C S. Tumor targeting by covalent conjugation of a natural fatty acid to paclitaxel. Clin Cancer Res. 2001 October; 7 (10):3229-38.). The ester can be solubilized and combined with an antioxidant and glucuronidation inhibitor, and formulated as an emulsion, SLN, or microencapsulated oil.

Example 3

Antioxidant Data

Figure 3:
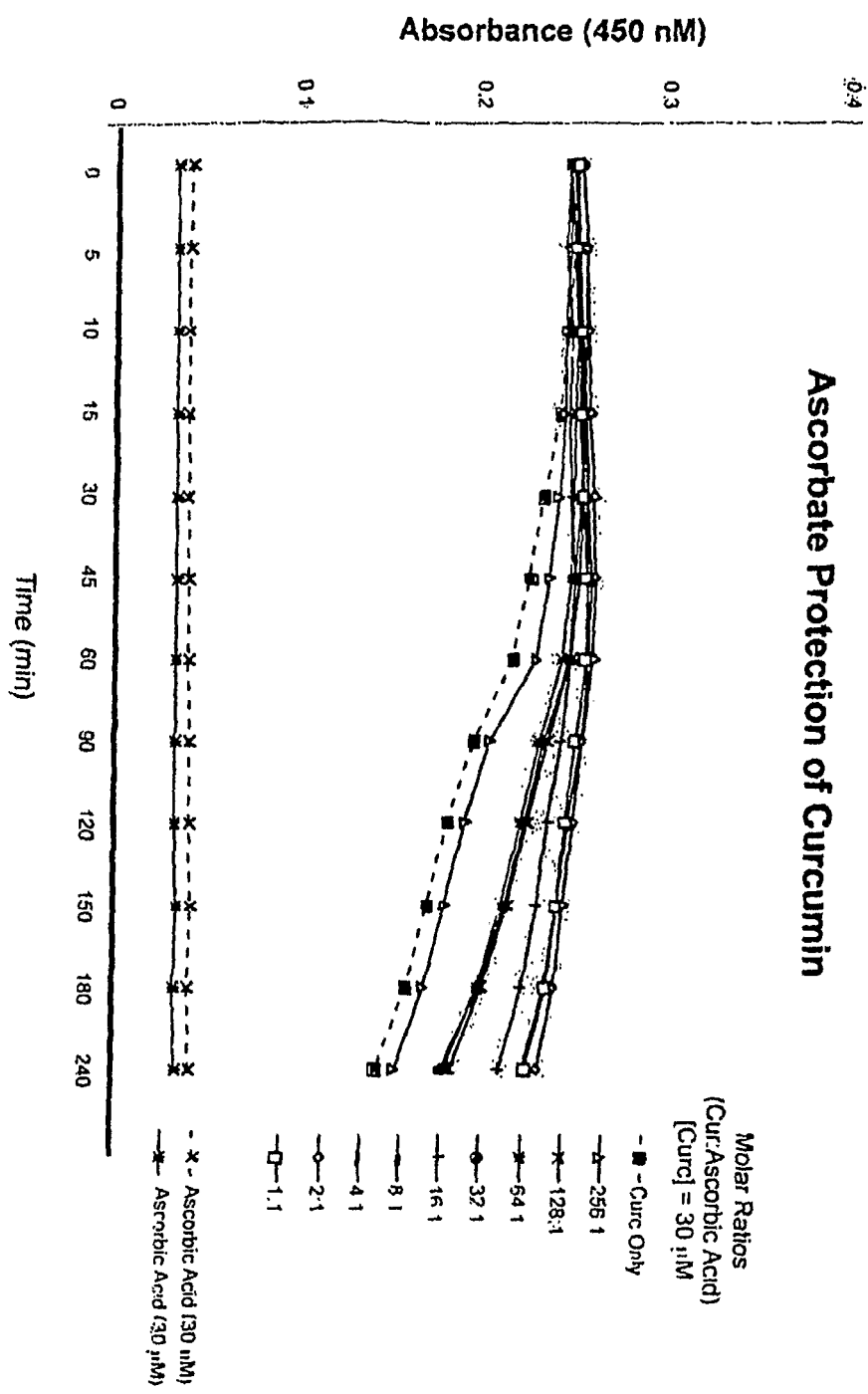
FIG. 3 is a graph of ascorbate concentration vs. time for various formulations of curcumin and ascorbate, at 450 nm.
Figure 4:
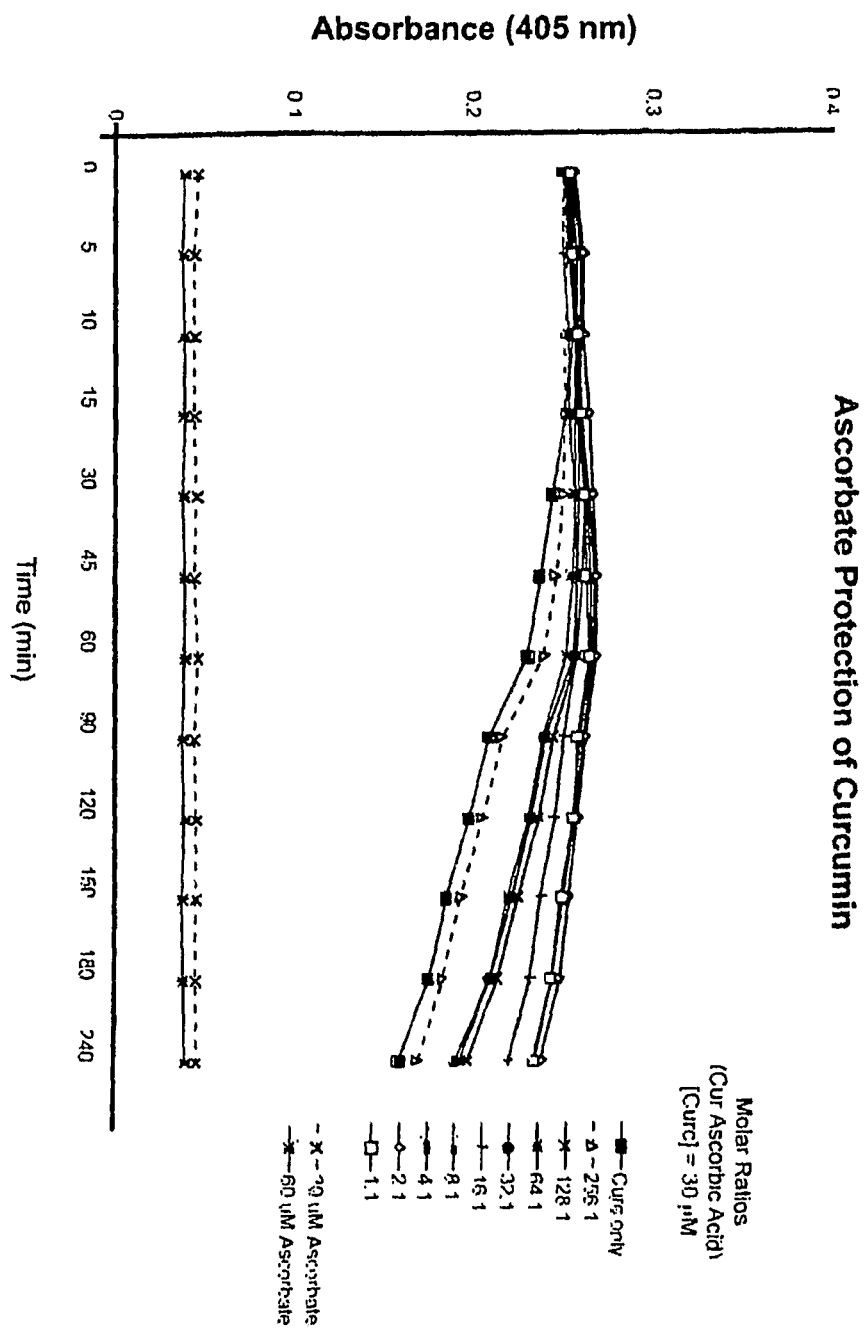
FIG. 4 is a graph similar to FIG. 3, but with absorbance measured at 405 nm.
Figure 6:
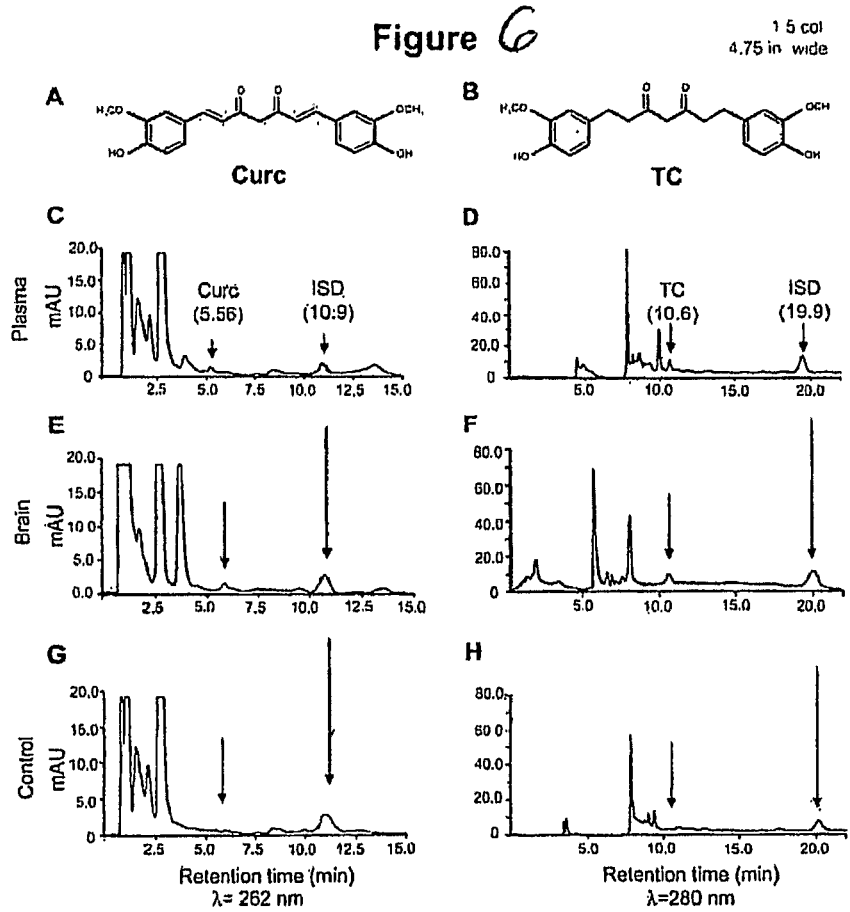
FIG. 6 shows structures of Curc and TC and HPLC chromatographs of Curc and TC in plasma or brain as indicated after injection, according to embodiments of the present invention.
Figure 7:
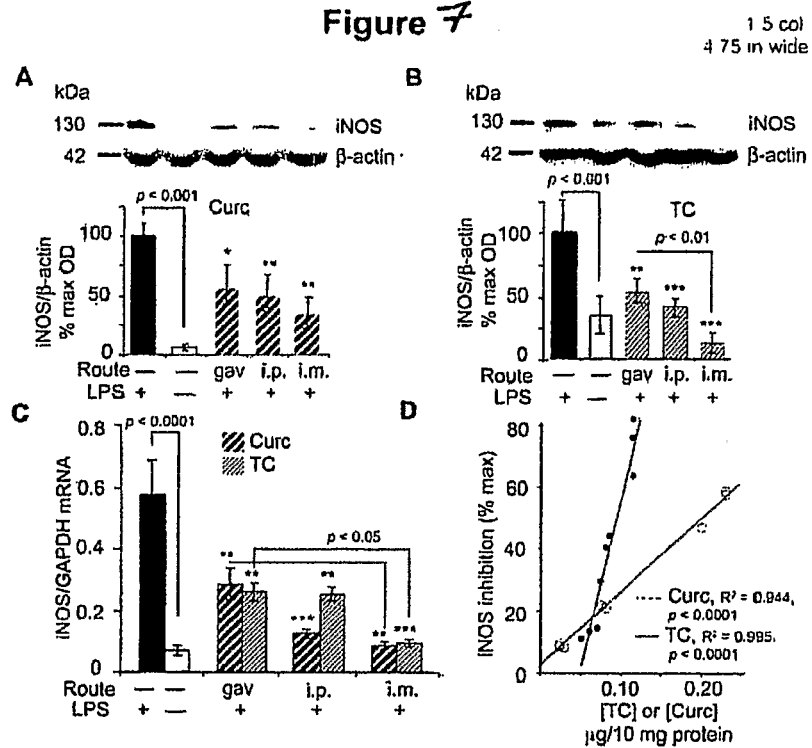
FIG. 7 shows quantification of inducible nitric oxide synthase (iNOS) protein and iNOS mRNA in brains of mice after administration of Curc or TC as indicated, according to embodiments of the present invention.
Figure 8:
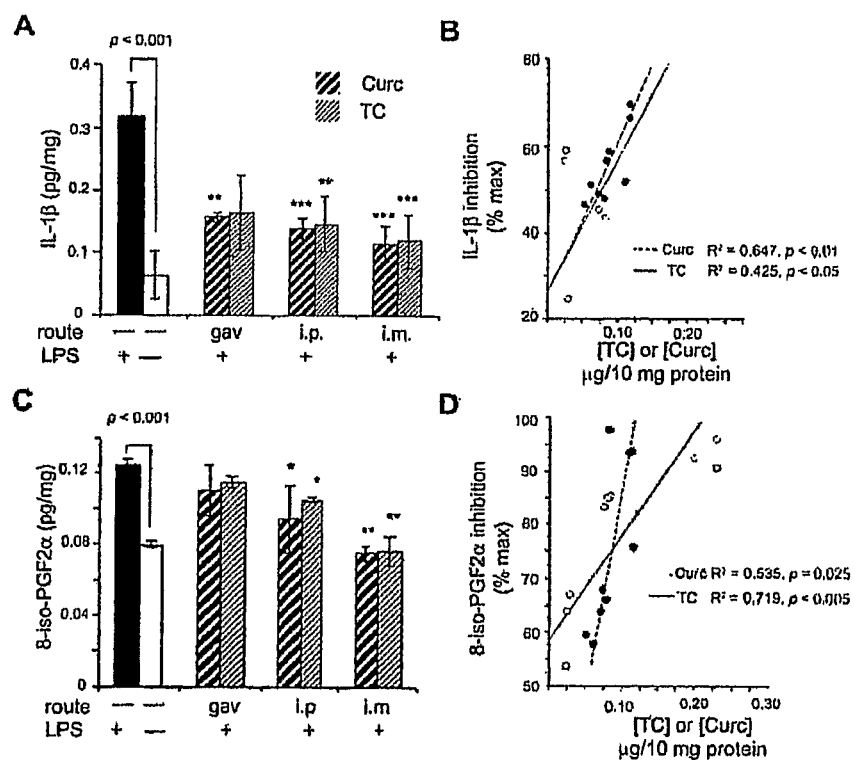
FIG. 8 shows quantification of interleukin 1 β (IL-1β) in mouse brain homogenates in mice pre-treated with or without Curc or TC as indicated, according to embodiments of the present invention.
Figure 10:
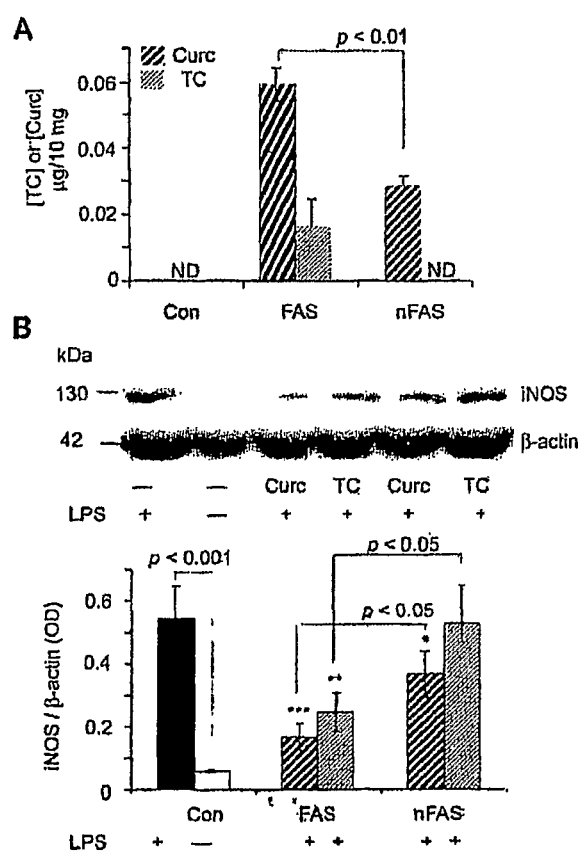
FIG. 10 shows quantification of Curc or TC in mouse brains after administration of Curc or TC to fasting (FAS) or non-fasting (nFAS) mice, according to embodiments of the present invention.
Figure 11:
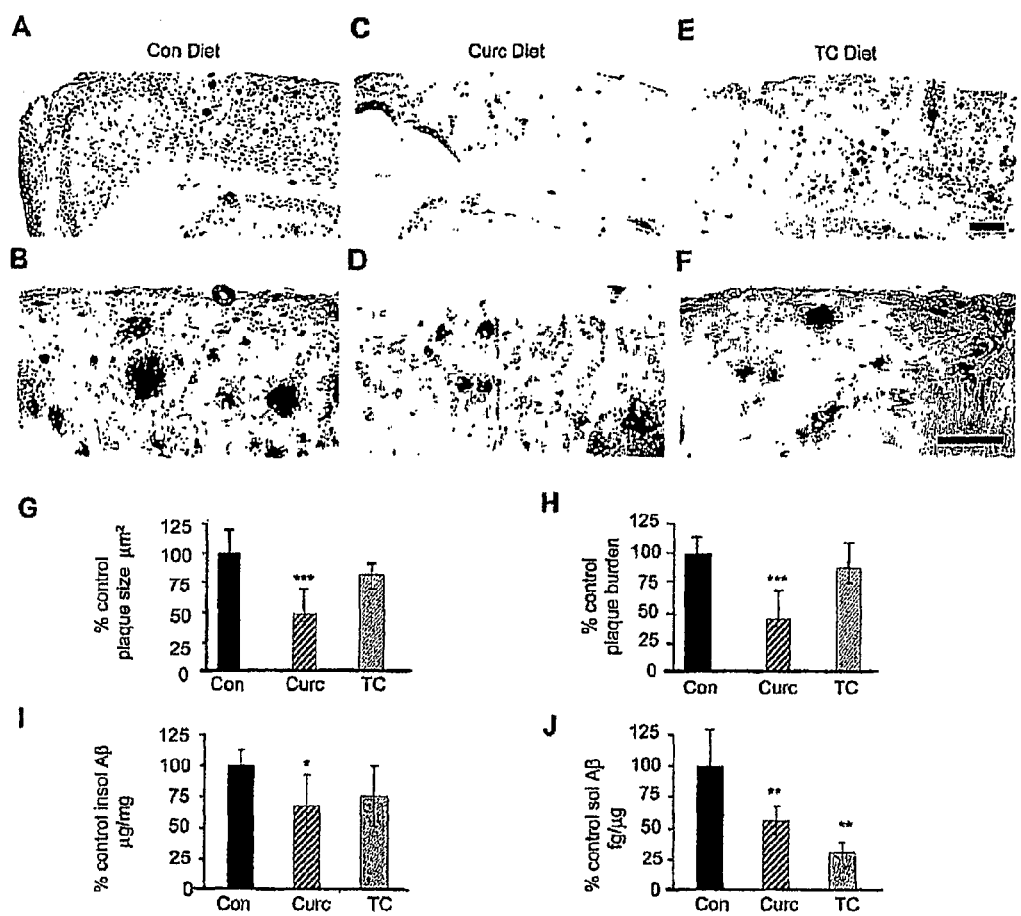
FIG. 11 shows micrographs of mouse brain homogenates stained with antibodies to Aβ (beta amyloid protein) from mice given a Curc, TC, or control (Con) diet for four months, as indicated, according to embodiments of the present invention.
Figure 13:
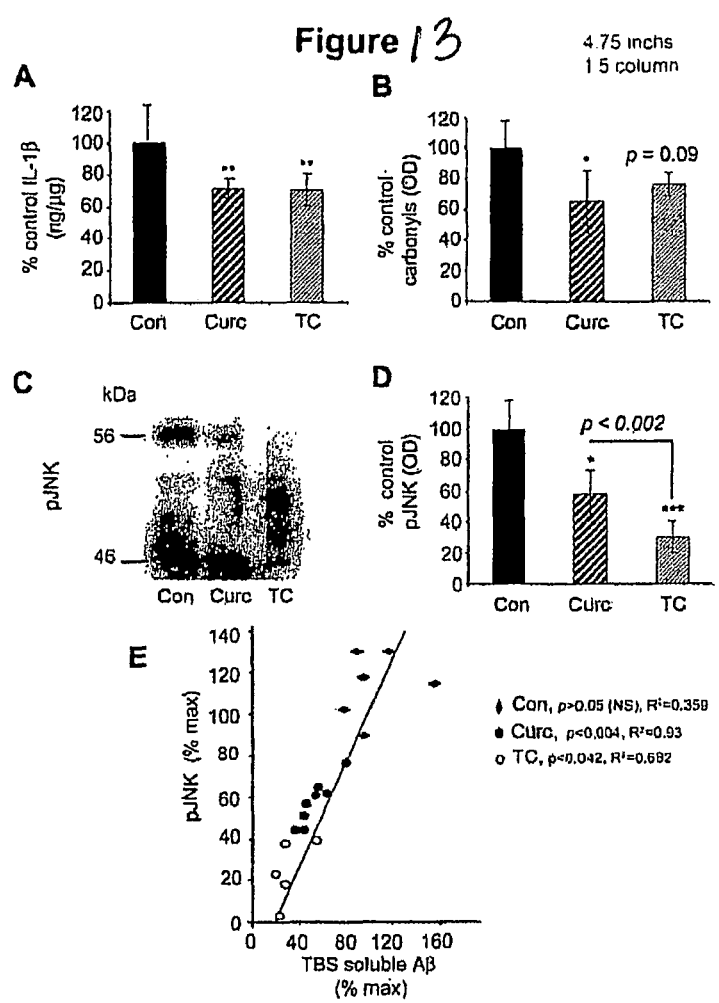
FIG. 13 shows quantification of IL-1β, phosopho c-jun n-terminal kinase (pJNK), and carbonyls in mouse brain homogenates from control fed Tg+ mice (Con), mice fed Curc (Curc), or mice fed TC (TC), according to embodiments of the present invention.
Figure 14:
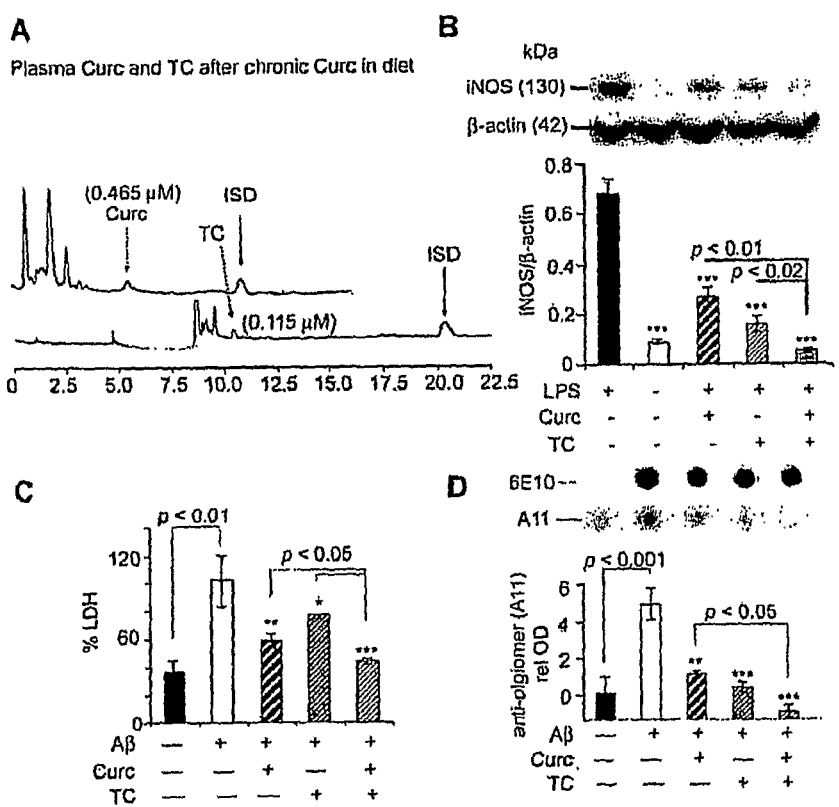
FIG. 14 shows quantification using chromatograms to detect Curc and TC in plasma from mice fed Curc for 4 months; quantification of iNOS in primary cortical neuron cultures treated with lipopolysaccharide (LPS) with or without Curc, TC, or Curc and TC; quantification of prior exposure to Curc and/or TC on Aβ42 oligomer-induced neuroblastoma cell death measured by LDH in media; and quantification of prior exposure to Curc and/or TC on pre-aggregated oligomers in a cell-free assay, according to embodiments of the present invention.

To test the effect of an antioxidant on curcumin stability, various 25 micromolar curcumin solutions were prepared, with or without an antioxidant (ascorbic acid or etrahydrocurcumin. Using absorbance spectroscopy, the intensity of curcumin's absorbance at 426 nm was measured. The results are presented in FIG. 2. "PBS" stands for phosphate buffered saline (pH 7.4); "Curc" denotes curcumin; "TC" denotes tetrahydrocurcumin; "Veh" denotes vehicle. The data shows that ascorbic acid is very effective at substantially retarding curcumin hydrolysis. Additional antioxidant data is presented in FIGS. 3 and 4, which show microplate reader absorbance data at 450 and 405 nm, respectively (flanking curcumin's absorbance peak at 426 nm). The data shows that ascorbic acid is very effective at retarding hydrolysis of curcumin, at a curcumin-to-ascorbic acid ratio of 1:1 or even 2:1, with somewhat diminished effectiveness at higher ratios.

The Appendix provides additional data on the differential effects of curcumin and its metabolite, tetrahydrocurcumin. All references cited in the application are incorporated herein in their entirety.

The invention has been described with reference to various embodiments and examples, but is not limited thereto. Variations may be made without departing from the invention's scope, which is limited only by the appended claims and equivalents thereof.

TABLE 1

Curc and TC can be detected in brain after gav or injection, and in plasma only after injection.

| | | Curc | | TC | |
|---|---|---|---|---|---|
| Treatment | Dose µg | Plasma (µg/ml) | Brain (µg/10 mg protein) | Plasma (µg/ml) | Brain (µg/10 mg protein) |
| con | 0.0 | ND | ND | ND | ND |
| gav | 147.0 | ND | $0.042 \pm 0.023^a$ | ND | $0.027 \pm 0.002^a$ |
| i.p. | 147.0 | $0.127 \pm 0.035^d$ (0.345 µM) | $0.074 \pm 0.003^b$ | $0.847 \pm 0.019^a$ (2.302 µM) | $0.076 \pm 0.003^b$ |
| i.m. | 73.5 | $0.238 \pm 0.048^e$ (0.647 µM) | $0.116 \pm 0.009^d$ | $0.971 \pm 0.092^a$ (2.639 µM) | $0.223 \pm 0.023^c$ |

These data showed brain and plasma levels of Curc or TC 4 hr after administration (by gav, i.p., or i.m.). Data are presented as mean ± SD. Different superscript letters signify statistical difference of means from each other between columns (treatments) within rows or between rows (routes) within treatments. p < 0.05 SD; standard deviation; ND; not detectable

TABLE 2

After chronic Curc or TC administration in diet, respective plasma levels are readily detectable, particularly with TC

| Treatment | Dose in mg/kg chow (daily consumption mg/day) | Plasma (µg/ml) |
|---|---|---|
| con | 0.0 (0) | ND |
| Curc | 500 (2.5) | $0.035 \pm 0.014^a$ (0.095 µM) |
| TC | 500 (2.5) | $0.270 \pm 0.003^b$ (0.734 µM) |

APPsw mice were fed Curc or TC in chow at 500 ppm for 4 months prior to analyzing Curc or TC in plasma, respectively. Data are presented as mean ± SD. Different superscript letters signify statistical difference of means from each other, p < 0.001. SD; standard deviation, ND; not detectable.

What is claimed is:

1. A curcuminoid composition having enhanced oral bioavailability, comprising:
   a curcuminoid selected from the group consisting of curcumin, metabolites of curcumin, tetrahydrocurcumin, demethoxycurcumin, bisdemethoxycurcumin, curcumin esters, and mixtures thereof;
   an antioxidant in an amount sufficient to protect the curcuminoid from hydrolysis;
   a water-solubilizing, pharmaceutically acceptable carrier comprising phosphatidylcholine (PC), the water-solubilizing, pharmaceutically acceptable carrier being selected from the group consisting of lipid micelles, microemulsions and microencapsulated oils, the PC and the curcuminoid being present in the composition in a molar ratio of 1:3.33 to 6:1; and
   optionally a glucuronidation inhibitor,
   wherein the composition is suitable for oral administration, and
   wherein the curcuminoid and the antioxidant are present in a weight ratio of about 10:1 or greater, and the curcuminoid composition is stable above pH 7.0.

2. The curcuminoid composition as recited in claim 1, wherein the curcuminoid is a curcumin ester comprising the esterification product of curcumin and a monocarboxylic acid.

3. The curcuminoid composition as recited in claim 2, wherein the monocarboxylic acid comprises an essential fatty acid.

4. The curcuminoid composition as recited in claim 3, wherein the essential fatty acid comprises an Omega-3 fatty acid.

5. The curcuminoid composition as recited in claim 4, wherein the Omega-3 fatty acid is docosahexaenoic acid.

6. The curcuminoid composition as recited in claim 1, wherein the lipid micelles are formed from one or more fatty acids, phospholipids, bile acids, edible oils, mixtures thereof, and/or pharmaceutically acceptable salts, hydrates, or conjugates thereof.

7. The curcuminoid composition as recited in claim 1, wherein the carrier comprises lipid micelles that are formed at least in part of phosphatidyl choline, deoxycholate, and taurocholate or other surfactants.

8. The curcuminoid composition as recited in claim 1, wherein the lipid micelles comprise an oil selected from the group consisting of olive oil, canola oil, fish oil, and mixtures thereof.

9. The curcuminoid composition as recited in claim 1, wherein the carrier comprises microencapsulated particles.

10. The curcuminoid composition as recited in claim 1, wherein the antioxidant is selected from the group consisting of ascorbic acid, acylated fat soluble ascorbic acid, vitamin C, alpha-lipoic acid, N-acetylcysteine, reduced glutathione, tetrahydrocurcumin, and mixtures thereof.

11. The curcuminoid composition as recited in claim 1, wherein the antioxidant comprises ascorbic acid.

12. The curcuminoid composition as recited in claim 1, wherein the antioxidant is both water-soluble and lipid-soluble.

13. The curcuminoid composition as recited in claim 1, wherein the glucuronidation inhibitor is selected from the group consisting of tetrahydrocurcumin, piperine, probencid, diclofenac, and mixtures thereof.

14. The curcuminoid composition as recited in claim 1, wherein the composition has the form of a microemulsion, solid lipid nanoparticles, microencapsulated particles, or gel, and is suitable for parenteral or enteral administration.

15. A curcuminoid composition having enhanced oral bioavailability, comprising:
a curcuminoid selected from the group consisting of curcumin tetrahydrocurcumin, and mixtures thereof;
phosphatidylcholine (PC), the PC and the curcuminoid being present in the composition in a molar ratio of 1:3.33 to 6:1;
docosahexaenoic acid; and
an antioxidant in an amount sufficient to protect the curcuminoid from hydrolysis;
wherein the composition is provided as a plurality of micelles,
wherein the composition is suitable for oral administration, and
wherein the curcuminoid and the antioxidant are present in a weight ratio of about 10:1 or greater, and the curcuminoid composition is stable above pH 7.0.

16. A curcuminoid composition having enhanced oral bioavailability, comprising:
curcumin;
phosphatidylcholine (PC), the PC and the curcumin being present in the composition in a molar ratio of 1:3.33 to 6:1;
docosahexaenoic acid; and
an antioxidant in an amount sufficient to protect the curcumin from hydrolysis;
wherein the composition is provided as a plurality of micelles,
wherein the composition is suitable for oral administration, and
wherein the curcumin and the antioxidant are present in a weight ratio of about 10:1 or greater, and the curcuminoid composition is stable above pH 7.0.

17. The curcuminoid composition of claim 1, wherein the curcuminoid comprises a curcumin ester and docosahexaenoic acid.

18. The curcuminoid composition as recited in claim 1, provided as solid lipid nanoparticles having an internal phase lipid, the curcuminoid, a surfactant, and a cosurfactant.

19. The curcuminoid composition as recited in claim 18, wherein the internal phase lipid is selected from the group consisting of triacylglycerols, tricaprin, trilaurin, trimyristin, tripalmitin, tristearin; acylglycerols, glycerol monostearate, glycerol behenate, glycerol palmitostearate; fatty acids, stearic acid, palmitic acid, decanoic acid, behenic acid; waxes, cetyl palmitate; cyclic complexes, cyclodextrin, para-acyl-calix-arenes; and mixtures thereof.

20. The curcuminoid composition as recited in claim 18, wherein the surfactant is selected from the group consisting of phospholipids, soy lecithin, egg lecithin, phosphatidylcholine; ethylene oxide/propylene oxide copolymers, Poloxamer 188, Poloxamer 182, Poloxamer 407, Poloxamine 908; sorbitan ethylene oxide/propylene oxide copolymers, Polysorbate 20, Polysorbate 60, Polysorbate 80; alkylaryl polyether alcohol polymers, tyloxapol.

21. The curcuminoid composition as recited in claim 18, wherein the co-surfactant is selected from the group consisting of sodium cholate, sodium glycocholate, sodium taurocholate, and sodium taurodeoxycholate.

22. A method of treating a neurodegenerative, age-related disease, comprising:
administering a therapeutically effective dose of a curcuminoid,
wherein the curcuminoid is provided as the curcuminoid of claim 1.

23. The method as recited in claim 22, wherein the therapeutically effective dose is sufficient to achieve a curcuminoid concentration in blood of 0.1-2 micromolar.

24. The curcuminoid composition as recited in claim 1, wherein the curcuminoid and the antioxidant are present in a ratio of about 8:1 to about 16:1.

* * * * *